United States Patent
Taguchi et al.

(10) Patent No.: US 7,357,015 B2
(45) Date of Patent: Apr. 15, 2008

(54) GAS CONCENTRATION SENSOR, HYDROGEN PURIFICATION UNIT USING THIS AND FUEL CELL SYSTEM

(75) Inventors: Kiyoshi Taguchi, Osaka (JP); Takeshi Tomizawa, Ikoma (JP); Kunihiro Ukai, Ikoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 709 days.

(21) Appl. No.: 10/297,249

(22) PCT Filed: Apr. 20, 2001

(86) PCT No.: PCT/JP01/03424

§ 371 (c)(1),
(2), (4) Date: Dec. 4, 2002

(87) PCT Pub. No.: WO01/96846

PCT Pub. Date: Dec. 20, 2001

(65) Prior Publication Data

US 2003/0129463 A1   Jul. 10, 2003

(30) Foreign Application Priority Data

Jun. 5, 2000 (JP) .............................. 2000-167986
Jun. 5, 2000 (JP) .............................. 2000-167987

(51) Int. Cl.
  *G01N 21/00* (2006.01)
  *G01N 27/00* (2006.01)
  *G01N 31/00* (2006.01)
  *G01N 33/00* (2006.01)
  *H01M 8/00* (2006.01)

(52) U.S. Cl. .............. 73/25.01; 422/94; 422/95; 422/96; 422/97; 422/98; 422/83; 429/12; 429/13; 429/22; 429/50; 436/43; 436/149; 436/145; 73/1.01; 73/1.02; 73/23.2

(58) Field of Classification Search ............... 422/83, 422/94–98; 429/12, 13, 22, 50; 436/43, 436/149, 145; 73/1.01, 1.02, 23.2, 25.01
See application file for complete search history.

(56) References Cited

U.S. PATENT DOCUMENTS 1,908,202 A     5/1933   White (Continued)

FOREIGN PATENT DOCUMENTS

GB        1 427 515        3/1976

(Continued)

OTHER PUBLICATIONS

First Office Action, Nov. 19, 2004(w/English Translation).

(Continued)

*Primary Examiner*—Brian Sines
(74) *Attorney, Agent, or Firm*—McDermott Will & Emery LLP (57) ABSTRACT

In order to provide a step capable of reliably detecting a CO concentration in a reformed gas at low cost and a hydrogen purifier capable of fully exerting a function of a CO purifying catalyst, a gas concentration detector comprising a reaction chamber which has a catalyst layer and a gas temperature detector and capable of detecting the concentration of carbon monoxide in the gas by means of a signal of the temperature detector referring to a reformed gas passing along through the reaction chamber.

1 Claim, 2 Drawing Sheets

U.S. PATENT DOCUMENTS

| | | | |
|---|---|---|---|
| 2,751,281 A | | 6/1956 | Cohn |
| 4,325,912 A | * | 4/1982 | Sawa et al. .................... 422/95 |
| 5,612,012 A | * | 3/1997 | Soma et al. ................ 423/246 |
| 5,677,073 A | * | 10/1997 | Kawatsu ...................... 429/22 |
| 6,173,602 B1 | * | 1/2001 | Moseley .................... 73/31.06 |
| 6,383,670 B1 | * | 5/2002 | Edlund et al. ................ 429/20 |
| 6,429,019 B1 | * | 8/2002 | Goldstein et al. ........... 436/134 |
| 6,562,088 B2 | * | 5/2003 | Ukai et al. ................ 48/197 R |

FOREIGN PATENT DOCUMENTS

| | | |
|---|---|---|
| JP | 57-28364 | 7/1955 |
| JP | 52-49889 | 4/1977 |
| JP | 8-298129 | 11/1996 |
| JP | 10-302821 | 11/1998 |
| JP | 11-130406 | 5/1999 |
| JP | 2000-123846 | 4/2000 |
| JP | 2000-241375 | 9/2000 |
| WO | WO96/2826 | 2/1996 |

OTHER PUBLICATIONS

Supplementary Partial European Search Report Issued in Corresponding European Patent Application No. EP 01 92 1972, dated Sep. 22, 2006.

* cited by examiner

GAS CONCENTRATION SENSOR, HYDROGEN PURIFICATION UNIT USING THIS AND FUEL CELL SYSTEM

TECHNICAL FIELD

The present invention relates to a gas concentration detector and a hydrogen purifier. More specifically, it relates to an apparatus which is mainly composed of hydrogen to be used as a fuel for fuel cells and the like and detects the concentration of carbon oxide (CO) in a reformed gas containing CO, and the hydrogen purifier.

BACKGROUND ART

Hydrogen used for fuel cells and the like was conventionally generated by mixing steam with a hydrocarbon type fuel such as methane, propane, gasoline or kerosine, an alcohol type fuel such as methanol, or an ether type fuel such as dimethylether and bringing the mixed gas into contact with a heated reforming catalyst.

In general, the hydrocarbon type fuel is reformed at temperatures of 500 to 800° C. while the alcohol type fuel and ether type fuel are reformed at temperatures of 200 to 400° C. CO generates in the reforming; as the reforming temperature is higher, the concentration of CO generating rises. Particularly, when the hydrocarbon type fuel is used, the CO concentration of the reformed gas grows up to about 10% by volume. For this reason, CO and hydrogen are reacted to each other by using a CO shifting catalyst to lower the CO concentration to thousands of ppm to several % by volume.

Moreover, in the case of fuel cells which operate at low temperatures of 100° C. or lower such as solid polymer type fuel cells in vehicle-mounted or domestic uses, there is a possibility that a Pt catalyst used in the electrodes is poisoned with CO contained in the reformed gas. Therefore, the CO concentration needs to be removed to 100 ppm or less, preferably 10 ppm or less, before the reformed gas is supplied to the fuel cell. For this reason, a CO purifying unit in which a catalyst is filled is arranged in a hydrogen purifier and then CO is methanated or selectively oxidized after addition of trace amounts of air, thereby removing CO.

When CO is selectively oxidized for removal with a CO purifying catalyst, a noble metal catalyst such as Pt, Ru, Rh or Pd is mainly used. Oxygen in an amount one to three times larger than CO is required to sufficiently remove CO.

Herein, when the amount of hydrogen to be supplied for changing the amount of power generation of the fuel cell system or when a catalytic activity decreases to a certain degree after the long-duration operation of the apparatus, the CO concentration in the reformed gas changes. It is therefore necessary to detect the CO concentration in order to control the amount of oxygen to be an optimum value.

However, application of a generally-implemented technique for detecting the CO concentration from absorption of ray of light of infrared wavelength due to CO, or technique for detecting the CO concentration from a change in resistance due to absorption of CO, is difficult at present because it does not function stably in the reformed gas or the cost thereof is high.

It has thus been difficult to always keep the oxygen to be supplied to the CO purifying catalyst in an optimum volume. It has also been difficult at the time of start-up of the fuel cell system to determine whether the reformed gas can be supplied to the fuel cell or not even after sufficient removal of CO in the hydrogen purifier.

As thus been described, in the conventional technique, there is no step for detecting the CO concentration which is effective in the reformed gas, low-cost and reliable, making the CO purifying catalyst insufficiently exert the function thereof or necessitating a long-time standby operation of the fuel cell system before the start-up thereof at which the supply of the reformed gas to the fuel cell begins.

Accordingly, it is an object of the present invention to provide a step capable of reliably detecting the CO concentration in the reformed gas at low cost, and to provide a hydrogen purifier with the function of the CO purifying catalyst in full play.

DISCLOSURE OF INVENTION

The present invention relates to a gas concentration detector comprising: a gas supply unit for supplying gas containing at least hydrogen; a reaction chamber which has a catalyst layer and is arranged on the downstream side of the gas supply unit; and a temperature detector for detecting a temperature of the catalyst layer and/or a temperature of gas after passage though the catalyst layer, characterized in that the concentration of carbon monoxide contained in the gas after passage through the catalyst layer is detected by means of a signal of the temperature detector.

In this gas concentration detector, it is effective that the reaction chamber is kept at a constant temperature.

It is also effective that a first temperature detector is arranged on the upstream side of the catalyst layer and a second temperature detector is arranged on the downstream side of the catalyst layer.

It is further effective that the catalyst layer contains at least Pt, Ru, Rh, Pd or Ni as a component having an activity.

It is further effective that the gas concentration detector further comprises a second gas supply unit for supplying oxgen-contained gas.

It is further effective that the gas concentration detector comprises a control unit for controlling a flow rate of oxygen-contained gas which is supplied from the second gas supply unit and changing a detecting range of concentration of carbon monoxide by adjusting a flow rate of oxygen-contained gas.

The present invention also relates to a hydrogen generator comprising: a carbon monoxide purifying unit; a oxygen-contained gas supply unit; and a gas temperature detector which is arranged on the upstream side and/or the downstream side of the carbon monoxide purifying unit, characterized in that the concentration of carbon monoxide contained in gas after passage through the carbon monoxide purifying unit is detected by means of a signal of the gas temperature detector, and a flow rate of the oxygen-contained gas is controlled in correspondence with the concentration of the carbon monoxide In this hydrogen purifier, it is effective that a temperature of the carbon monoxide purifying unit is controlled in correspondence with the concentration of the carbon monoxide.

The present invention also relates to a fuel cell system comprising: a hydrogen purifier; a fuel cell; and a gas temperature detector which is arranged between the hydrogen purifier and the fuel cell, characterized in that the concentration of carbon monoxide contained in gas to be introduced from the hydrogen purifier to the fuel cell is detected by means of a signal of the gas temperature detector, and introduction of the gas to the fuel cell is stopped by switching a gas flow path connecting the hydrogen purifier and the fuel cell in correspondence with the concentration of the carbon monoxide.

BEST MODE FOR CARRYING OUT THE INVENTION

Figure 1:
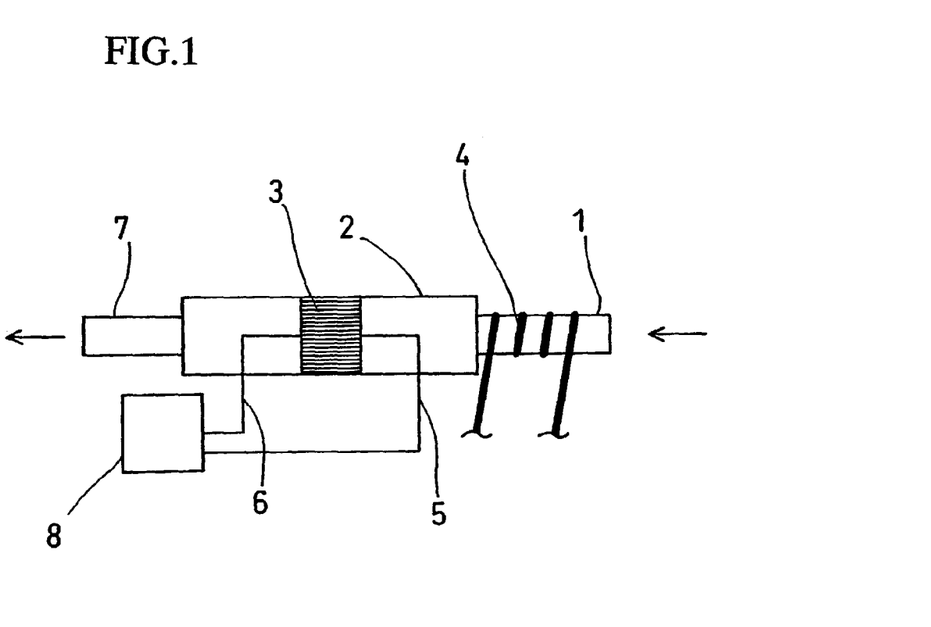
FIG. 1 is a schematic view showing a configuration of one embodiment of a gas concentration detector in accordance with the present invention.

In the following, Embodiment 1 of the present invention will be described with reference to the drawings:

FIG. 1 is a schematic view showing a configuration of a gas concentration detector in accordance with Embodiment 1 of the present invention. In FIG. 1, a reformed gas supplied from a reformed gas inlet 1 (a gas containing at least hydrogen and carbon monoxide) is sent out to a reaction chamber 2, reacts in a catalyst layer 3 and is then discharged from out of a reformed gas outlet 7. A temperature upstream from the catalyst layer and a temperature downstream therefrom are measured on a first thermocouple 5 which is a first temperature detector and on a second thermocouple 6 which is a second temperature detector, respectively. Signals from these thermocouples are sent to a signal treatment device 8, to be output as a CO concentration.

Further, a heater 4 keeps the reaction chamber 2 at a constant temperature. Herein, a case of a reformed gas obtained when a natural gas is steam-reformed (the CO concentration is 10 to 1000 ppm, the concentration of carbon dioxide is about 20%, and that of hydrogen is the remaining %) will be described: It is to be noted that even when a gas having a different composition is used, there will be no essential change in the effect produced by using the gas concentration detector in accordance with the present invention as long as the gas contains extra amount of hydrogen to CO.

Next, a principle of operation of the gas concentration detector in accordance with the present invention will be described: In the catalyst layer 3, carbon monoxide and hydrogen in the reformed gas react to each other to generate methane and steam. A reaction heat then is about 200 kJ per 1 mol of CO, and a heating value on the catalyst changes corresponding to the CO concentration. A change in temperatures due to the heat generation is detected to measure the CO concentration.

Figure 2:
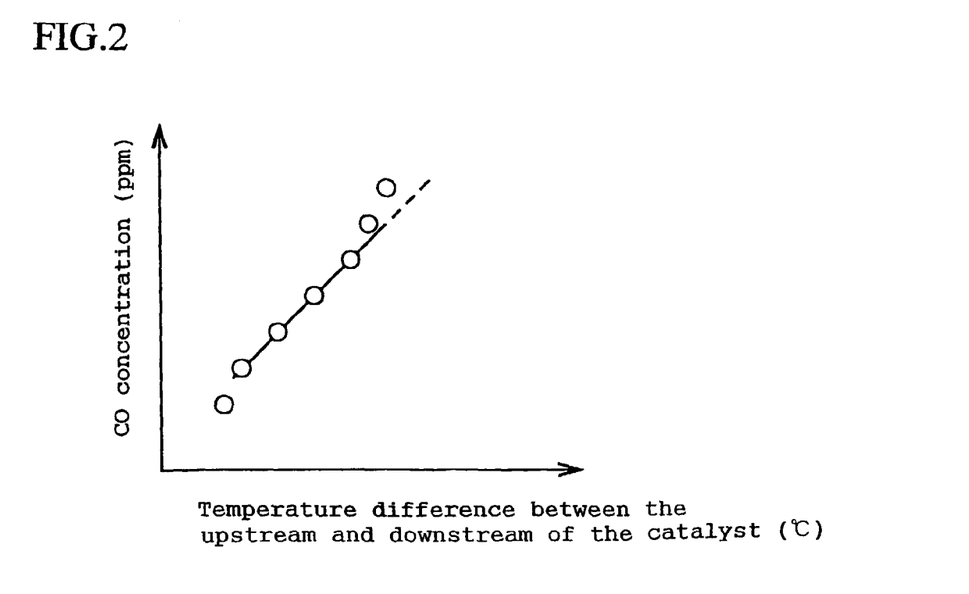
FIG. 2 is a diagram showing the characteristic of the gas concentration detector in accordance with the present invention shown in FIG. 1.

FIG. 2 shows a relation between a difference between temperatures detected with the first thermocouple 5 and the second thermocouple 6 ($\Delta t$), and the CO concentration in the reformed gas. In a region where the CO concentration and the temperature difference can be expressed by a fixed relational expression, the CO concentration can be detected by drawing a calibration curve, as expressed in a solid line in FIG. 2. When the CO concentration is substantially high, a conversion rate of CO decreases, and thereby the change in the temperature difference versus the CO concentration becomes small, making the detection of the CO concentration difficult. In this case, raising the temperature of the reaction chamber 2 allows an increase in the CO conversion rate so that a threshold concentration to be detected can be made high.

However, since carbon dioxide is methanized when the temperature of the reaction chamber 2 becomes high, it is of necessity to use the reaction chamber 2 at such a temperature that heat generation due to the methanization of $CO_2$ has no influence. The temperature of the reaction chamber 2, therefore, is preferably about 250° C. or lower, while it depends on a kind of the catalyst.

On the contrary, when the CO concentration is low, the heating value on the catalyst becomes small, and thereby a change in the temperature difference becomes small, making the detection of the CO concentration difficult. In such a case, interrupting heat dissipation to the outside of the reaction chamber 2 or increasing the value of the heat generation on the catalyst by accelerating the flow of the reformed gas enables detection of CO with further lower concentrations.

Moreover, as for a component having a catalytic activity for use in the catalyst layer 3, one selectively shows activity to the methanation of CO can be used. That is to say, between carbon dioxide and CO in the reformed gas, a catalytic component showing an activity only to hydrogeneration of CO, or a catalytic component selectively showing an activity to the hydrogeneration of CO.

Such a catalytic component can be exemplified by metals such as Pt, Ru, Rh, Pd and Ni. It is preferable that the catalyst layer 3 contains, particularly, at least Ru, Rh or Ni as the catalytic component.

As for a carrier of the catalytic component used for the catalyst layer 3, there is no particular limitation and one capable of carrying the catalytic component in a highly dispersing state may be applied. Such a carrier may be exemplified by alumina, silica, silica-alumina, magnesia, titania and zeolite.

As for a substrate to be used for the catalyst layer 3, one capable of securing a sufficient area where the catalytic component is in contact with the gas in the reaction chamber may be used. Such a substrate is preferably one in the form of honeycomb or one in the form of form with communicating pores, and one in the form of pellet may also be applied.

That is to say, in the present invention, a catalyst is made by having a carrier carry the catalytic component, which is then adhered to the substrate to obtain the catalyst layer 3. In a case of using the substrate in the pellet form, a column, for example, may be arranged within the reaction chamber 2 and filled with the pellet carrying the catalytic component thereon. At that time, the carrier on the form of pellet can be used as it is as the substrate in the form of pellet.

Furthermore, the preferable temperature of the catalyst layer is 80° C. or higher at which CO can react sufficiently, and 250° C. or lower at which $CO_2$ is resistant to reacting. It should be noted that an operation temperature can be determined as appropriate according to applications so that the calibration curve can be drawn in a condition including a side reaction.

Moreover, for the accurate detection of the heat generation on the catalyst, it is preferable that the temperature of the reaction chamber 2 is not influenced by the external environment, and that heat is sufficiently insulated so as to control the temperature to be constant.

While the heater is used here for the temperature control, a thermal medium such as a cooling fan or oil may be applied. In an application where highly accurate detection of CO is not required, there is no need of the temperature control.

While, in FIG. 1, the thermocouple is used for detecting the temperature of the catalyst layer, another detecting means such as thermistor may be used as long as it can detect the temperature.

Further, while the temperatures on the upstream side and the downstream side of the catalyst layer are detected here, when the temperature of the reformed gas to be supplied is constant, even measurement of only the temperature on the downstream side of the catalyst layer makes it possible to measure the CO concentration with accuracy.

The gas concentration detector using the gas temperature detector thus described can also be applied to a hydrogen purifier and a fuel cell system. Also on the downstream sides of a shifting unit and a purifying unit constituting the hydrogen purifier, for example, adoption of the similar configuration to the above-mentioned reaction chamber permits detection of the CO concentrations of gas flowing out of the shifting unit to the purifying unit and gas flowing out of the purifying unit.

For example, the gas temperature detector is arranged on the upstream side of the CO purifying catalyst and by means of a signal of the gas temperature detector, the CO concentration is determined, corresponding to which air is controlled to be supplied in an appropriated amount, thereby inhibiting needless consumption of hydrogen as well as preventing a rise in the CO concentration on the downstream side of the purifying catalyst attributed to an air shortage. With the gas concentration detector used for the fuel cell system, accordingly, improvement of the effectiveness and the stable operation thereof can be secured.

Additionally, also when the gas temperature detector is disposed on the downstream side of the CO purifying catalyst, the similar effect to the case where the disposal is made on the upstream side can be obtained by controlling the amount of the air such that the CO concentration on the downstream side of the purifying catalyst does not increase.

Furthermore, in a case where the gas concentration detector is applied to the fuel cell system comprising the hydrogen purifier and the fuel cell, the gas temperature detector is arranged midway between the hydrogen purifier and the fuel cell, and when the CO concentration detected by the signal of the gas temperature detector is high, the gas flow path is closed to prevent introduction of the reformed gas to the fuel cell or is switched to discharge the reformed gas out of the fuel cell, leading to prevention of the fuel cell from being poisoned with CO.

In addition, because the sufficient removal of CO can be detected in the hydrogen purifier at the time of the startup, the standby operation, which is conducted until the temperature of the purifying catalyst rises to a temperature for the normal operation in which the purifying catalyst can remove CO with certainty, or the like is not necessary, permitting a prompt power generation.

Since the catalyst used herein is one obtained by applying the function of the CO purifying catalyst to the gas concentration detector, detection of temperature of part of the CO purifying catalyst also allows the detection of the CO concentration. When there is a big change in the temperature and it is not caused by the change in the CO concentration, the detection of the CO concentration with sufficient accuracy is not possible and, therefore, a condition where the flow rate of the reformed gas and the temperature vary in a small degree is preferable.

Figure 3:
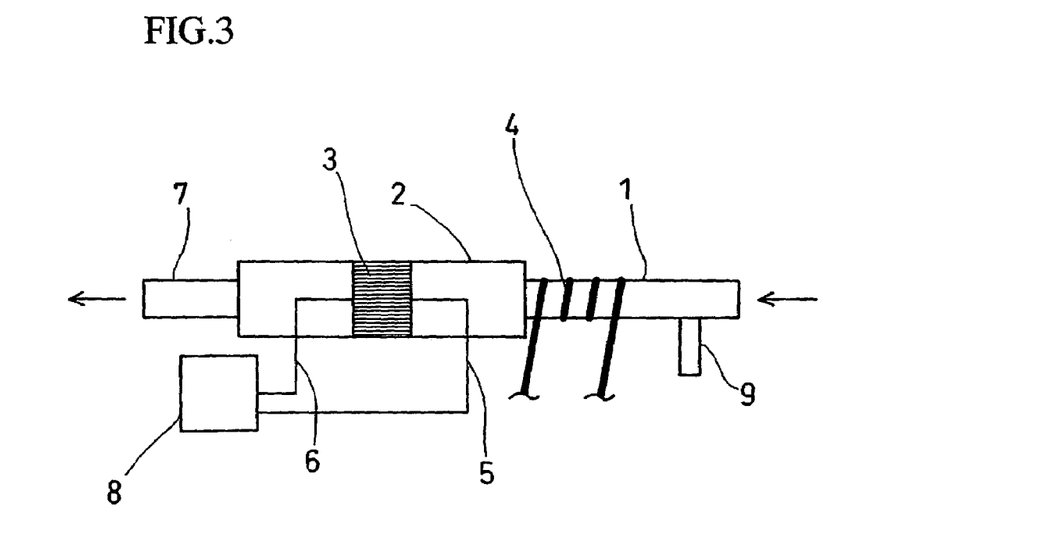
FIG. 3 is a schematic view showing a configuration of one embodiment of another gas concentration detector in accordance with the present invention.

Next, Embodiment 2 of the present invention will be described with reference to the drawings:

FIG. 3 is a schematic view showing a configuration of a gas concentration detector in accordance with Embodiment 2 of the present invention. In FIG. 3, a reformed gas supplied from a reformed gas inlet 1 is sent out to a reaction chamber 2, reacts in a catalyst layer 3 and is then discharged from out of a reformed gas outlet 7. A temperature upstream from the catalyst layer and a temperature downstream therefrom are measured on a first thermocouple 5 which is a first temperature detector and on a second thermocouple 6 which is a second temperature detector, respectively. Signals from these thermocouples are sent to a signal treatment device 8, to be output as a CO concentration.

Further, a heater 4 keeps the reaction chamber 2 at a constant temperature. A air supply unit 9 is arranged on the upstream side of the reaction chamber 2. In the present embodiment, a case of a reformed gas obtained when a natural gas is steam-reformed by the reformed gas (the CO concentration is 10 to 10000 ppm, the concentration of carbon dioxide is 20%, and that of hydrogen is the remaining %) will be described: It is to be noted that even when a gas having a different composition is used, there will be no essential change in the effect produced by using the gas concentration detector in accordance with the present invention as long as the gas contains extra amount of hydrogen to CO.

Next, a principle of operation of the gas concentration detector in accordance with the present invention will be described: In the catalyst layer 3, oxygen supplied by the air supply unit 9 oxidizes CO or hydrogen to generate a heat. The heating value then corresponds to heat generated in the oxidization of hydrogen and CO, which are about 240 kJ per 1 mol of hydrogen and about 290 kJ per 1 mol of CO.

It is known that because CO is prone to be absorbed into a noble metal, the surface of the noble metal is completely covered with CO when the ratio thereof to oxygen is high, to serve a function of inhibiting the oxidizations of hydrogen and CO. For this reason, in a case where a fixed amount of oxygen is supplied to gradually increase the CO concentration, the oxidization is inhibited when the CO concentration has reached a certain level, lowering the temperature of the catalyst layer 3. The CO concentration with which the temperature decrease begins is determined by the amount of oxygen being supplied. The CO concentration can be detected, therefore, by having drawn a calibration curve showing a relation between the amount of the supplied oxygen and the CO concentration with which the temperature of the catalyst begins to decrease. The optical amount of oxygen contained in air supplied from the air supply unit 9 is one to three times larger than the CO concentration to be detected.

Figure 4:
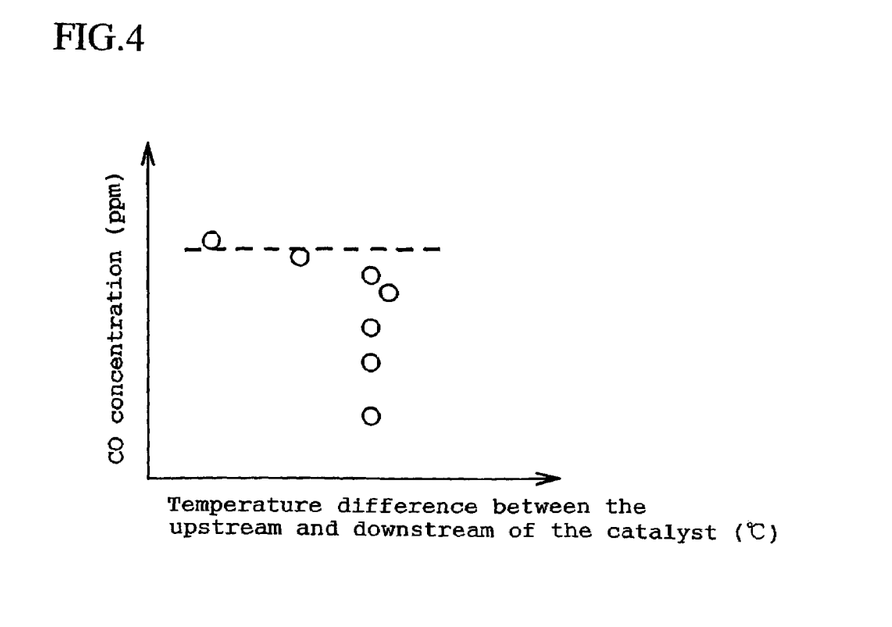
FIG. 4 is a diagram showing the characteristic of the gas concentration detector in accordance with the present invention shown in FIG. 3.

Herein, FIG. 4 shows a relation between the CO concentration and a difference between temperatures upstream and downstream from the catalyst layer 3 ($\Delta t$), in the present embodiment. When the CO concentration becomes a fixed value or larger, the oxidizations of CO and hydrogen in the catalyst layer 3 are inhibited, resulting in an abrupt decrease in the difference between the temperatures upstream and downstream from the catalyst detected by the first thermocouple 5 and the second thermocouple 6, respectively. Because the CO concentration then is determined from the amount of the air supplied from the air supply unit 9, the amount of the air is set in advance in correspondence with the CO concentration to be detected.

Moreover, since a change in the amount of the supplied air allows a change in the CO concentration with which the temperature change occurs, CO with various concentrations can be detected.

It is to be noted that the separator layer 3 may be the same one as mentioned in Embodiment 1 above.

Further, an operating temperature and the amount of the supplied air may be in ranges where the oxidization is inhibited when the CO concentration becomes the CO concentration to be detected or higher and the temperature change appears clearly. The lower the temperature, the higher absorptivity of CO into the catalyst, and the stronger the function of inhibiting the oxidization. Accordingly, the lower the temperature, the lower the concentration of CO can be detected. On the contrary, with the higher temperature, the effect of inhibiting the oxidization on the catalyst attributed to the absorption of CO becomes smaller, increasing the CO concentration with which the temperature change occurs. Besides, the CO concentration with which the temperature change occurs changes corresponding to the amount of the air to be supplied. When the amount of oxygen is small to CO, the oxidization is inhibited with ease, permitting the detection of CO concentration in a low level.

Moreover, for the accurate detection of the heat generation on the catalyst, it is preferable that the temperature of the reaction chamber 2 is not influenced by the external environment, and that heat is sufficiently insulated so as to control the temperature to be constant.

While the heater is used here for the temperature control, a thermal medium such as a cooling fan or oil may be applied. In an application where highly accurate detection of CO is not required, there is no need of the temperature control.

While, in FIG. 3, the thermocouple is used for detecting the temperature of the catalyst layer, another detecting means such as thermistor may be used as long as it can detect the temperature.

Additionally, while the temperatures on the upstream side and the downstream side of the catalyst layer are detected here, when the temperature of the reformed gas to be supplied is constant, even measurement of only the temperature on the downstream side of the catalyst layer makes it possible to measure the CO concentration with accuracy.

Furthermore, by arranging the gas temperature detector in accordance with the present invention on the upstream side of the CO purifying catalyst and controlling the air to be supplied in an appropriate amount, in correspondence with the detected CO concentration, needless consumption of hydrogen is inhibited and a rise in the CO concentration on the downstream side of the purifying catalyst attributed to an air shortage is avoided, securing the effectiveness and the stable operation of the fuel cell.

In addition, also when the gas temperature detector is disposed on the downstream side of the CO purifying catalyst, the similar effect to the case where the disposal is made on the upstream side can be obtained by controlling the amount of the air such that the CO concentration on the downstream side of the purifying catalyst does not increase.

The gas concentration detector in accordance with the present invention can be applied not only to a reformer of the hydrogen purifier but also to a shifter, a purifier and a fuel cell system.

For example, the gas concentration detector is arranged midway between the hydrogen purifier and the fuel cell, and when the CO concentration detected is high, the gas flow path is switched to prevent the reformed gas from passing along through the fuel cell, leading to prevention of the fuel cell from being poisoned with CO. In addition, because the sufficient removal of CO can be detected with the hydrogen purifier at the time of the startup, the standby operation, which is conducted until the temperature of the purifying catalyst rises to a temperature for the normal operation at which the purifying catalyst can remove CO with certainty, or the like is not necessary, enabling a prompt power generation.

Since the catalyst used in the above embodiment is one obtained by applying the function of the CO purifying catalyst to the gas concentration detector, detection of temperature of part of the CO purifying catalyst also allows the detection of the CO concentration. When there is a big change in the temperature and it is not caused by the change in the CO concentration, the detection of the CO concentration with sufficient accuracy is not possible and, therefore, a condition where the flow rate of the reformed gas and the temperature vary in a small degree is preferable.

Next, in the following the gas concentration detector in accordance with the present invention will be described more specifically, using examples: It should be noted that the present invention is not limited to these.

EXAMPLE 1

The reaction chamber 2 in the gas concentration detector shown in FIG. 1 was filled with a catalyst which is an almina pellet having a diameter of 1 mm and a length of 1 mm with 5% by weight of Ru carried thereon. A reformed gas composed of 20% by volume of carbon dioxide and the remaining t by volume of hydrogen was supplied from the reformed gas inlet at a flow rate of 0.1 liter per minute and the temperature of the first thermocouple was controlled to be 150° C. in the heater 4. A reformed gas, mixed with CO such that the CO concentrations in the reformed gas were 5 ppm, 20 ppm, 100 ppm, 500 ppm, 900 ppm, 1200 ppm and 2000 ppm, was supplied and the temperatures of the first thermocouple and the second thermocouple were measured. The results of measurements of the CO concentrations (ppm) as well as the temperature differences between the upstream and the downstream (° C.) were shown in Table 1.

TABLE 1

| CO concentration (ppm) | Temperature difference between upstream/downstream Δt (° C.) |
|---|---|
| 0 | 0 |
| 5 | 0.1 |
| 20 | 1 |
| 100 | 5 |
| 500 | 25 |
| 900 | 45 |
| 1200 | 55 |
| 2000 | 70 |

EXAMPLE 2

A reformed gas, mixed with CO such that the CO concentrations in the reformed gas were 1 ppm, 4 ppm, 20 ppm, 100 ppm, 180 ppm, 240 ppm and 400 ppm, was supplied and the temperatures of the first thermocouple and the second thermocouple were measured in the same manner as in Example 1, except that the flow rate of the reformed gas was increased to 0.3 liter per minute. The results were shown in Table 2.

TABLE 2

| CO concentration (ppm) | Temperature difference between upstream/downstream Δt (° C.) |
|---|---|
| 0 | 0 |
| 1 | 0.2 |
| 4 | 1 |
| 20 | 6 |
| 100 | 29 |
| 180 | 46 |
| 240 | 56 |
| 400 | 73 |

EXAMPLE 3

A reformed gas, mixed with CO such that the CO concentrations in the reformed gas were 0 ppm, 5 ppm, 20 ppm, 100 ppm, 500 ppm, 900 ppm, 1200 ppm and 2000 ppm, was supplied and the temperature of the first thermocouple and the second thermocouple were measured in the same manner as in Example 1, except that Rh was carried in place of Ru. The results were shown in Table 3.

TABLE 3

| CO concentration (ppm) | Temperature difference between upstream/downstream Δt (° C.) |
|---|---|
| 0 | 0 |
| 5 | 0.1 |
| 20 | 1 |
| 100 | 4 |
| 500 | 23 |
| 900 | 44 |
| 1200 | 54 |
| 2000 | 69 |

EXAMPLE 4

A reformed gas, mixed with CO such that the CO concentrations in the reformed gas were 0 ppm, 5 ppm, 100 ppm, 500 ppm, 900 ppm, 1200 ppm and 2000 ppm, was supplied and the temperatures of the first thermocouple and the second thermocouple were measured in the same manner as in Example 1, except that Ni was carried in place of Ru. The results were show in Table 3.

TABLE 4

| CO concentration (ppm) | Temperature difference between upstream/downstream Δt (° C.) |
|---|---|
| 0 | 0 |
| 5 | 0.1 |
| 20 | 1 |
| 100 | 4 |
| 500 | 22 |
| 900 | 43 |
| 1200 | 53 |
| 2000 | 67 |

EXAMPLE 5

The reaction chamber 2 in the gas concentration detector shown in FIG. 3 was filled with a catalyst which is an almina pellet having a diameter of 1 mm and a length of 1 mm with 5% by weight of Pt carried thereon. A reformed gas composed of 20% by volume of carbon dioxide and the remaining % by volume of hydrogen was supplied from the reformed gas inlet 1 at a flow rate of 0.1 liter per minute and air was supplied from the air supply unit 9 such that the concentration of oxygen was 0.15% by volume. The temperature of the first thermocouple 5 was controlled to be 150° C. in the heater 4. A reformed gas, mixed with CO such that the CO concentrations in the reformed gas were 100 ppm, 500 ppm, 700 ppm, 1000 ppm, 1200 ppm, 1500 ppm and 2000 ppm, was supplied and the temperatures of the first thermocouple 5 and the second thermocouple 6 were measured. The results of measurements of the CO concentrations (ppm) as well as the temperature differences between the upstream and the downstream (° C.) were shown in Table 5.

TABLE 5

| CO concentration (ppm) | Temperature difference between upstream/downstream Δt (° C.) |
|---|---|
| 100 | 30 |
| 500 | 31 |
| 700 | 33 |
| 1000 | 29 |
| 1200 | 15 |
| 1500 | 10 |
| 2000 | 3 |

EXAMPLE 6

A reformed gas, mixed with CO such that the CO concentrations in the reformed gas were 1500 ppm, 1800 ppm, 2000 ppm, 2200 ppm, 2500 ppm and 3000 ppm, was supplied and the temperatures of the first thermocouple 5 and the second thermocouple 6 were measured in the same manner as in Example 5, except that the air mixed in the reformed gas was in such an amount that the concentration of oxygen was 0.3% by volume. The results were shown in Table 6.

TABLE 6

| CO concentration (ppm) | Temperature difference between upstream/downstream Δt (° C.) |
|---|---|
| 1500 | 60 |
| 1800 | 62 |
| 2000 | 62 |
| 2200 | 28 |
| 2500 | 15 |
| 3000 | 8 |

EXAMPLE 7

A reformed gas, mixed with CO such that the CO concentrations in the reformed gas were 100 ppm, 500 ppm, 700 ppm, 1000 ppm, 1200 ppm 1500 ppm and 2000 ppm, was supplied and the temperatures of the first thermocouple 5 and the second thermocouple 6 were measured in the same manner as in Example 5, except that Ru was carried in place of Pt. The results were shown in Table 7.

TABLE 7

| CO concentration (ppm) | Temperature difference between upstream/downstream Δt (° C.) |
| --- | --- |
| 100 | 32 |
| 500 | 33 |
| 700 | 35 |
| 1000 | 31 |
| 1200 | 17 |
| 1500 | 12 |
| 2000 | 4 |

INDUSTRIAL APPLICABILITY

As obvious from the results of evaluations of the gas concentration detectors in the above examples, according to the present invention, the CO concentration in the reformed gas can be detected by detecting the temperature of the catalyst.

The invention claimed is:

1. A method for detecting the concentration of carbon monoxide using a hydrogen purifier comprising: a carbon monoxide purifying unit including a catalyst layer having activity for methanation; an oxygen-contained gas supply unit; and a gas temperature detector which is arranged on the upstream side and/or the downstream side of said carbon monoxide purifying unit, said method comprising the steps of:

setting the temperature of said catalyst layer to 80 to 250° C.; and detecting the concentration of carbon monoxide contained in gas after passage through said carbon monoxide purifying unit by means of a signal of said gas temperature detector.

* * * * *

UNITED STATES PATENT AND TRADEMARK OFFICE
CERTIFICATE OF CORRECTION

| | | |
|---|---|---|
| PATENT NO. | : 7,357,015 B2 | Page 1 of 1 |
| APPLICATION NO. | : 10/297249 | |
| DATED | : April 15, 2008 | |
| INVENTOR(S) | : Kiyoshi Taguchi et al. | |

It is certified that error appears in the above-identified patent and that said Letters Patent is hereby corrected as shown below:

On the title page of the patent, in Item "(54)" and col. 1, lines 1-3, change the title from "GAS CONCENTRATION SENSOR, HYDROGEN PURIFICATION UNIT USING THIS AND FUEL CELL SYSTEM" to --GAS CONCENTRATION DETECTOR, HYDROGEN PURIFIER AND FUEL CELL SYSTEM USING THE SAME--.

Signed and Sealed this

Seventh Day of October, 2008

JON W. DUDAS
*Director of the United States Patent and Trademark Office*